(12) United States Patent
Okamoto et al.

(10) Patent No.: US 6,705,728 B2
(45) Date of Patent: Mar. 16, 2004

(54) OPHTHALMOLOGIC APPARATUS

(75) Inventors: Tadashi Okamoto, Tokyo (JP); Mitsuaki Wada, Tokyo (JP); Takeyuki Kato, Tokyo (JP); Masaki Ohno, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 237 days.

(21) Appl. No.: 09/820,928

(22) Filed: Mar. 30, 2001

(65) Prior Publication Data

US 2001/0028441 A1 Oct. 11, 2001

(30) Foreign Application Priority Data

Mar. 31, 2000 (JP) .......................................... 2000-099476

(51) Int. Cl.$^7$ ................................................ A61B 3/10
(52) U.S. Cl. ........................................................ 351/221
(58) Field of Search .................... 396/18, 324; 351/205, 351/206, 213, 214, 216, 221

(56) References Cited

U.S. PATENT DOCUMENTS

| | | | | |
|---|---|---|---|---|
| 4,662,731 A | * | 5/1987 | Robert et al. ................ | 351/214 |
| 4,799,783 A | * | 1/1989 | Takahashi et al. ........... | 351/206 |
| 5,255,025 A | * | 10/1993 | Volk ............................ | 351/205 |
| 5,995,759 A | * | 11/1999 | Kohayakawa ................ | 396/18 |
| 6,086,205 A | * | 7/2000 | Svetliza ....................... | 351/221 |
| 6,327,375 B1 | * | 12/2001 | Matsumoto et al. ........ | 351/211 |

* cited by examiner

*Primary Examiner*—Dennis W. Ruhl
*Assistant Examiner*—John R. Sanders
(74) *Attorney, Agent, or Firm*—Armstrong, Kratz, Quintos, Hanson & Brooks, LLP (57) ABSTRACT

In order to observe a front eye portion of an eye (E) to be examined, when a frame is moved to within a first region to approach the eye E to be examined, a stereo angle converting portion as means for shifting an optical path and a color temperature converting element (61) as optical converting means are removed from right and left optical axes (L1 and L2). On the other hand, in order to observe an eye fundus portion of the eye (E) to be examined, when the frame is moved to within a second region to leave the eye (E) to be examined, the stereo angle converting portion and the color temperature converting element (61) are disposed on the right and left optical axes (L1 and L2).

11 Claims, 6 Drawing Sheets

Prior Art

OPHTHALMOLOGIC APPARATUS

BACKGROUND OF THE INVENTION

1. Field of the Invention

The present invention relates to an ophthalmologic apparatus such as a slit lamp microscope with a binocular stereomicroscope used in such as an observation or a photographing with respect to an eye to be examined, of a person to be examined.

2. Description of the Related Art

Generally, a stereomicroscope is applied to a wide area such as a medical field, an industrial field and the like. An object of its use is in an ophthalmologic field to finely perform an observation and an examination with respect to an eye of a person to be examined as well as to observe an eye and the like of a person to be examined, which is an observation object, with magnification. Thus, a stereomicroscope by which an examiner can observe and examine an eye of a person to be examined, in a comfortable position, is desired.

For example, a conventional binocular stereomicroscope used in a slit lamp microscope is constructed by, an objective lens unit, a variable power optical system unit for making variable power with respect to an observation light flux passed through the objective lens unit, an imaging lens for obtaining an observation image by imaging the observation light flux for which the variable power is made in a predetermined position, an erecting prism for erecting the observation image obtained by the imaging lens, and an eyepiece unit having an eyepiece.

Such a stereomicroscope has, for example, a fixed stereo angle of 13° approximately. By using the stereomicroscope, it is possible to perform a stereo view with the above fixed stereo angle for cornea, conjunctiva and front vitreous body (hereinafter refereed to as "front eye portion") of a person to be examined. On the other hand, when retina and back vitrous body (hereinafter referred to as "eye fundus portion" of a person to be examined are examined, a lens is further provided. However, when a binocular field of view with a a stereo angle of 13° and such becomes is extremely narrow.

Also, according to a binocular stereomicroscope described in Japanese Patent Publication No. Hei 7-111507, a stereo angle converter with a rotatable optical main body is provided between an objective lens and a variable power converter corresponding to the above variable power optical system unit. A relative position of an optical axis of a partial light beam is shifted by the rotatable optical main body of the stereo angle converter to convert a stereo angle into other stereo angles, so that an eye front portion and an eye fundus portion of a person to be examined can be observed. That is, when the rotatable optical main body is rotated by, for example, 90°, the distance between the right and left optical paths (axes) of a partial light beam is short in a region between the optical main body and the objective lens. Thus, a stereo angle is made small by the rotation of the optical main body.

However, when an eye fundus of a person to be examined is observed, conventionally, an ophthalmoscope such as an erected microscope or an inverted microscope, an eye fundus camera, a slit lamp, a scan type laser apparatus or the like is used. The slit lamp is indispensable in an ophthalmic field, and is a commonly used instrument which may be referred to even as a stethoscope in ophthalmology. In particular, when a slit lamp microscope with a non-contact front lens is used, an observation of an eye fundus portion is extremely simplified. Also, a non-contact observation does not make a person to be examined uncomfortable. Thus, such an eye fundus observation is widely performed in a daily ophthalmic examination. Also, an optical property of the objective lens is extremely improved, and a following eye fundus portion observation of a person to be examined is performed by a slit lamp microscope with the front lens.

(1) The eye funds portion observation is carried out by operating the slit lamp microscope in such a manner as the front focus of the front lens is focused with the back focus of the objective lens of the slit lamp microscope while holding the front lens by the examiners hands.

(2) In stead of holding the front lens by hand, the front lens is held by a holding device for holding the front lens to perform the eye fundus portion observation.

However, in a conventional stereomicroscope, a microscope portion having, an objective lens unit, a variable power optical system unit, an imaging lens, an erecting lens and an eyepiece unit with an eyepiece, and a microscope arm portion for supporting the microscope portion are combined with each other, so that a stereo angle is fixed. When carrying out a stereoscopic observation of the eye funds portion, the field of view become narrow necessarily for observing either a front eye portion or an eye fundus portion of a person to be examined.

Also, in the above stereomicroscope described in Japanese Patent Publication No. Hei 7-111507, the rotatable optical main body of the stereo angle converter is rotated to convert a stereo angle into other stereo angle, so that an eye front portion and an eye fundus portion in a person to be examined can be observed. However, when the eye front portion and the eye fundus portion in the person to be examined are observed using this stereomicroscope, in order to obtain a stereo angle required in respective portions, it is necessary to rotate the optical main body by respective accurate rotation angles and then to hold it. If the optical main body cannot be accurately held with a rotation angle required to obtain a predetermined stereo angle for observing, for example, the front eye portion, of an eye of a person to be examined, a center of the field of view is shifted for observing the front eye portion of the person to be examined, so that inconvenience in observation of the front eye portion of the eye to be examined occurs. Also, since a slight shift in the rotation angle of the optical main body influences accuracy of an optical axis, it is difficult to adjust a rotation angle of the optical main body.

Furthermore, in the eye fundus portion observation with the above objective lens, this operation is complicated and is largely dependent on an experience of an examiner, so that the eye fundus portion observation takes a long time and a burden is imposed on an examiner and a person to be examined.

SUMMARY OF THE INVENTION

The present invention has been made in view of the above circumstance, and an object of the present invention is to provide a binocular stereomicroscope in which a stereo angle converting unit having a stereo angle converting portion for performing a stereo angle conversion is provided, and which easily selects a predetermined stereo angle and can easily observe and examine a front eye portion and an eye fundus portion in a person to be examined by inserting or removing the stereo angle converting portion of the stereo angle converting unit onto or from the right and left optical axes if necessary.

By the way, when an ophthalmologic apparatus such as a slit lamp microscope having such a stereomicroscope is used, an arrangement position of the stereomicroscope in the case where the front eye portion of the eye to be examined is observed is different from that of the stereomicroscope in the case wherein the eye fundus portion is observed. Thus, when the stereo angle conversion is performed by the above stereo angle converting portion, it is necessary to move a frame in which the stereomicroscope is provided in a predetermined position. Here, an examiner observes an eye to be examined with respect to fifty persons or more per day in many cases. Thus, even if an adjustment operation time per person is short, a burden imposed on the examiner is increased in total.

Also, in the above ophthalmologic apparatus, for example, a halogen lamp is used as an illuminating light source for illuminating the eye to be examined. A color temperature of the reflection light (observation light) from the eye to be examined, illuminated by the halogen lamp, is suitable in the case where the front eye portion of the eye to be examined is observed, so that a preferable front eye portion image can be obtained. However, when the eye fundus portion of the eye to be examined is observed, since a color temperature of the observation light becomes too high, for example, a flare occurs in the obtained eye fundus image to make the image low in contrast.

And another object of the present invention is to provide an ophthalmologic apparatus which has a binocular stereomicroscope, in which a stereo angle converting unit and a color temperature converting element are provided, and in which an observation, a photographing and the like with respect to a front eye portion and an eye fundus portion in an eye to be examined can be performed fast and easy and optimized by a conversion of a color temperature of reflection light (observation light) from the eye of a person to be examined by the color temperature converting element together with a stereo angle conversion by the stereo angle converting unit in accordance with a front eye portion observation or an eye fundus portion observation.

According to a first aspect of the present invention, there is provided an ophthalmologic apparatus including, a stereomicroscope which is provided on a movable frame and in which observation light is divided into right and left optical axes between an objective lens and an eyepiece, and a halogen lamp as a light source, characterized by comprising: means for optically changing an optical path, which is provided on the right and left optical axes; and means for electrically and/or optically changing the observation light or reflection light, so that an image of a portion to be examined, of an eye is easily observed.

According to a second aspect of the present invention, there is provided an ophthalmologic apparatus including a binocular stereomicroscope which is provided on a movable frame and has right and left optical axes, characterized by comprising: stereo angle converting means for shifting a relative position of the right and left optical axes; position detecting means for detecting a position of the frame; and control means for controlling operation of the stereo angle converting means in accordance with a result by the position detecting means.

According to a third aspect of the present invention, there is provided an ophthalmologic apparatus comprising an illuminating means for illuminating an eye to be examined, and a binocular stereomicroscope with right and left optical axes, both of which are provided on a movable frame, characterized by comprising: stereo angle converting means for performing a stereo angle conversion by shifting a relative position of the right and left optical axes; color temperature converting means for performing a conversion of a color temperature of a reflection light from the eye to be examined which is illuminated by the illuminating means; position detecting means for detecting a position of the frame; and control means for controlling operations of the stereo angle converting means and the color temperature converting means in accordance with a result by the position detecting means.

According to a fourth aspect of the present invention, there is provided an ophthalmologic apparatus in which an auxiliary (front) lens is to be inserted onto or removed from an optical axes between an eye to be examined and an objective lens in accordance with the times of an eye funds portion observation or a front eye portion observation, of the eye to be examined, characterized by comprising: detecting means which is provided between the eye to be examined and the objective lens, for detecting an insertion of the auxiliary lens; and control means for controlling an insertion and a removal of the stereo angle converting means and/or the color temperature converting means in accordance with a result of the detecting means.

According to a fifth aspect of the present invention, there is provided an ophthalmologic apparatus characterized by comprising switching means for alternately switching light source voltage control between the front eye portion and the eye funds portion, in which the color temperature converting element is removed from an optical path of the light source when the light source voltage control is switched to the front eye portion, and the color temperature converting element is inserted onto the optical path of the light source when the light source voltage control is switched to the eye funds portion.

As described above, according to the present invention, the stereo angle conversion by the stereo angle converting unit and the conversion of the color temperature of the observation light by the color temperature converting element can be performed in accordance with the front eye portion observation or the eye fundus portion observation, so that the observation, the photographing and the like with respect to the front eye portion and the eye fundus portion in the eye to be examined can be performed fast and easy and optimized.

DETAILED DESCRIPTION OF THE PREFERRED EMBODIMENTS

Figure 1:
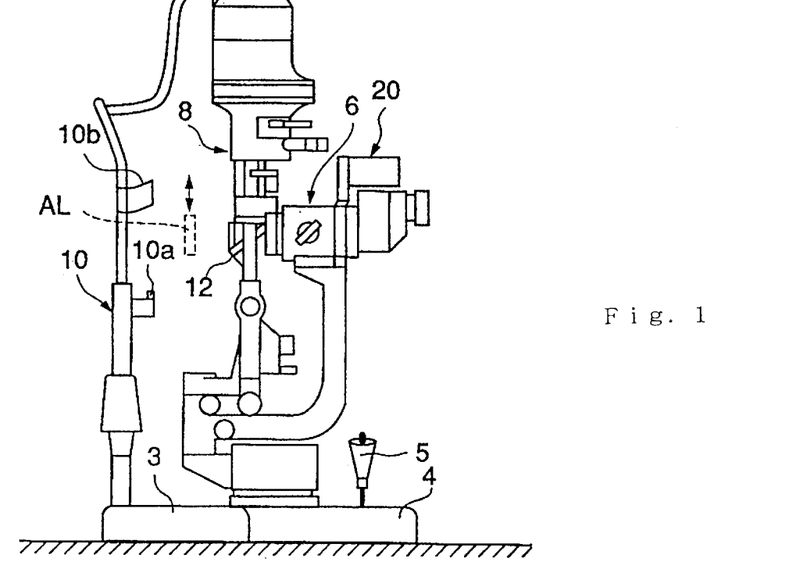
FIG. 1 is a side view representing an external structure of a slit lamp microscope which is one example of an ophthalmologic apparatus with a binocular stereomicroscope, according to an embodiment of the present invention.

FIG. 1 is a side view representing an external structure of a slit lamp microscope which is one example of an ophthalmologic apparatus with a binocular stereomicroscope, according to an embodiment of the present invention. As shown in FIG. 1, the ophthalmologic apparatus according to the embodiment of the present invention includes, a frame 4 which is set on, for example, a table (not shown) and movable on the surface of the table in a horizontal direction, an actuating mechanism portion 3 for actuating the frame 4 in the horizontal direction, a binocular stereomicroscope 6 for observing a front eye portion and an eye fundus portion of an eye of a person to be examined, a TV camera unit 20 detachable on the stereomicroscope 6, a chin rest portion 10 which is provided for holding the face of the person to be examined and has a chin rest 10a movable in the up and down direction and a forehead rest 10b, a mirror 12, and an illuminating unit 8 which is disposed to be orthogonal to the mirror 12 to illuminate the eye to be examined. And, a joystick 5 used as an operation lever for actuating the frame 4 by manual operation of an examiner is provided on the opposite side (examiner's side) of the chin rest portion 10 with respect to the stereomicroscope 6 on the frame 4.

Figure 2:
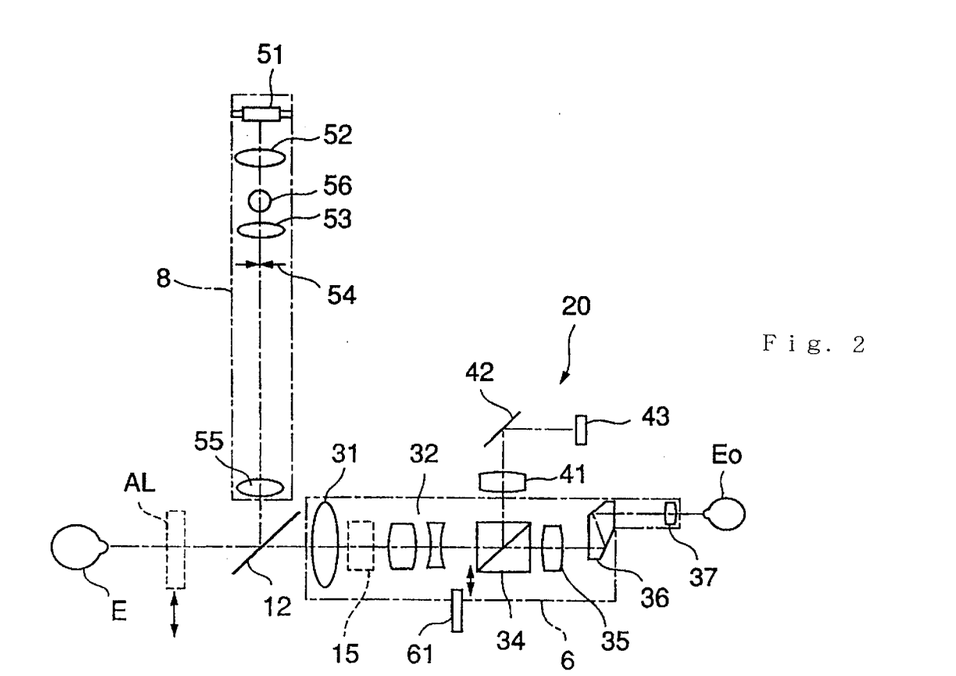
FIG. 2 is a side view representing a structure of an optical system of a slit lamp microscope which is one example of an ophthalmologic apparatus with a binocular stereomicroscope, according to an embodiment of the present invention.
Figures 3, 4:
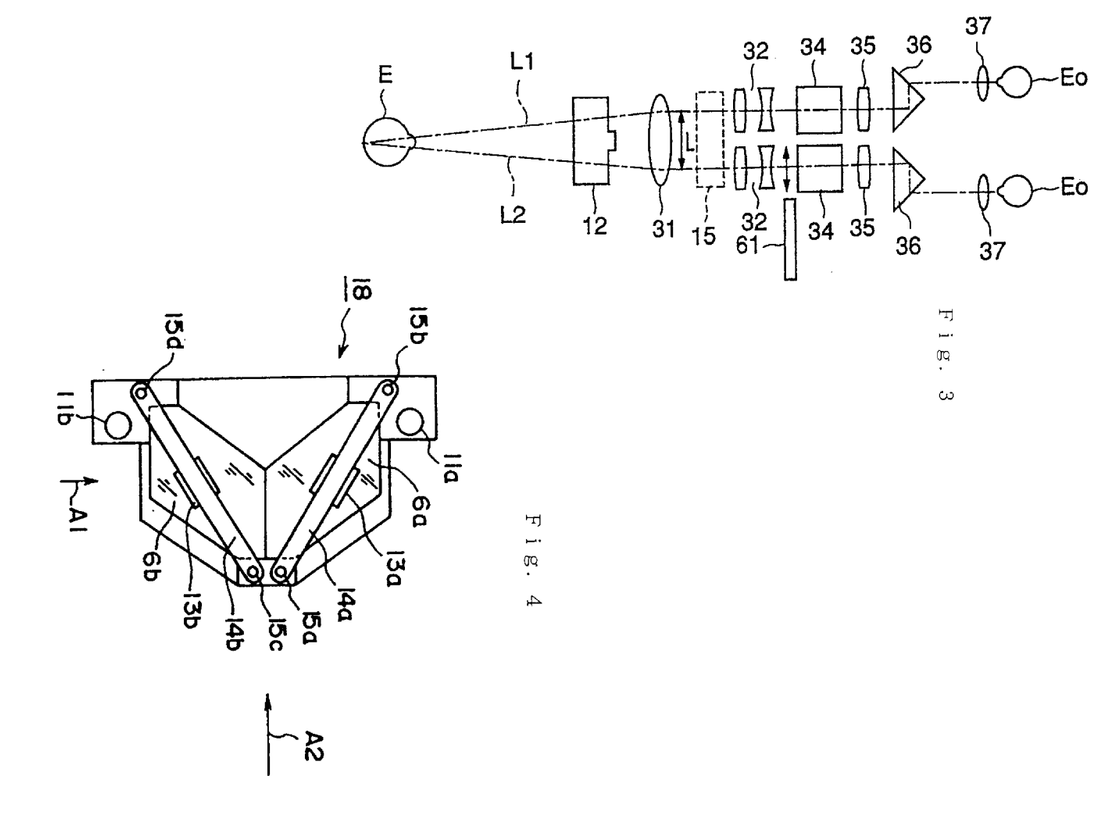
FIG. 3 is a side view representing a structure of an optical system of a slit lamp microscope which is one example of an ophthalmologic apparatus with a binocular stereomicroscope, according to an embodiment of the present invention.
FIG. 4 is a plan view representing a structure of a stereo angle converting portion of a stereo angle converting unit of the stereomicroscope according to a first embodiment of the present invention.

FIGS. 2 and 3 show structures of optical systems of a slit lamp microscope which is one example of the ophthalmologic apparatus with a binocular stereomicroscope according to the embodiment of the present invention. As shown in FIGS. 2 and 3, the stereomicroscope 6 is constructed by an objective lens 31, a stereo angle converting unit 15 for converting a stereo angle into other stereo angle by refracting two systems of observation lights (reflection lights from the eye E to be examined) passed through the objective lens 31 to shift a relational position of optical axes with respect to the right and left optical axes L1 and L2 with a distance L between the optical axes, a variable power optical system 32 for making variable power with respect to each of the two systems of the observation lights passed through the stereo angle converting unit 15, a color temperature converting element 61 which is provided to be insertable into and removable from the right and left optical axes L1 and L2 and optically converts a color temperature of the observation lights into other color temperature thereof in accordance with observation regions (front eye portion and eye fundus portion), a beam splitter 34 for branching the observation lights to the TV camera unit 20, a relay lens 35, a prism 36, and an eyepiece 37. By such a structure, the eye front portion and the eye fundus portion of the eye E to be examined can be observed from an examiner's eye Eo.

Also, the TV camera unit 20 is constructed by, a condenser lens 41 for condensing the observation light branched from the beam splitter 34 of the stereomicroscope 6, a reflection mirror 42 for reflecting the observation lights which passed through the condenser lens 41, and an image pickup element 43 for receiving the observation lights reflected by the reflection mirror 42. Thus, a front eye portion image or an eye fundus portion image, of the eye E to be examined is formed on the image pickup element 43.

Further, the illuminating unit 8 is constructed by, for example, a halogen lamp 51 used as a light source for observing the eye E to be examined, a condenser lens 52, for example, a xenon lamp 56 used as a light source for photographing the eye E to be examined, a condenser lens 53, a field stop 54 for passing only a portion of light from the condenser lens 53, a projective lens 55 for projecting the light passed through the field stop 54 as slit light to the eye E to be examined through the mirror 12.

A reference AL represented by a broken line in FIGS. 1 and 2 denotes an auxiliary lens which is inserted into optical axes between the eye E to be examined and the objective lens 31 in an eye fundus observation and constructed by a contact lens for canceling the power of a vitreous body of the eye to be examined. This auxiliary lens AL is removed from the right and left optical axes in a front eye portion observation, and can be inserted into or removed from the optical axes with a state that it is held by the examiner or by holding means provided in the vicinity of the forehead rest 10b in an eye fundus observation.

As described above, the stereo angle converting portion for converting a stereo angle into other stereo angle is inserted into or removed from the right and left optical axes of the observation light fluxes in accordance with a necessary stereo angle. Thus, in a normal observation (a stereo angle is α1), since the stereo angle converting portion is removed from the right and left optical axes in a position where the observation light fluxes are not shifted, an unnecessary optical member is not disposed on the right and left optical axes, so that a further distinct observation image can be obtained.

Figure 5:
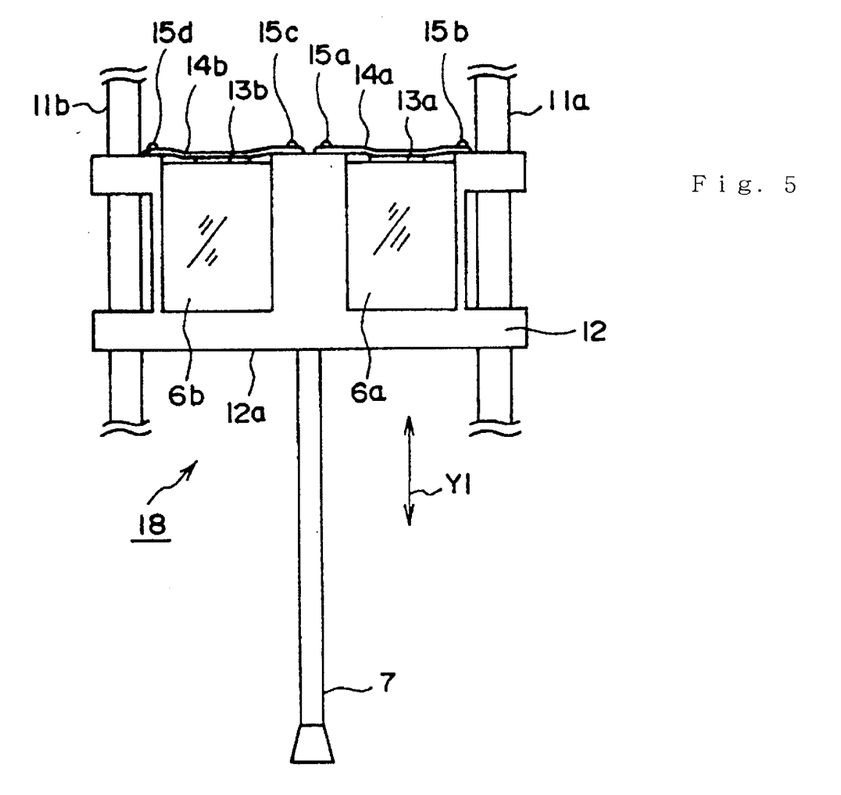
FIG. 5 is a side view representing the structure of the stereo angle converting portion of the stereo angle converting unit of the stereomicroscope according to the first embodiment of the present invention.
Figure 5A:
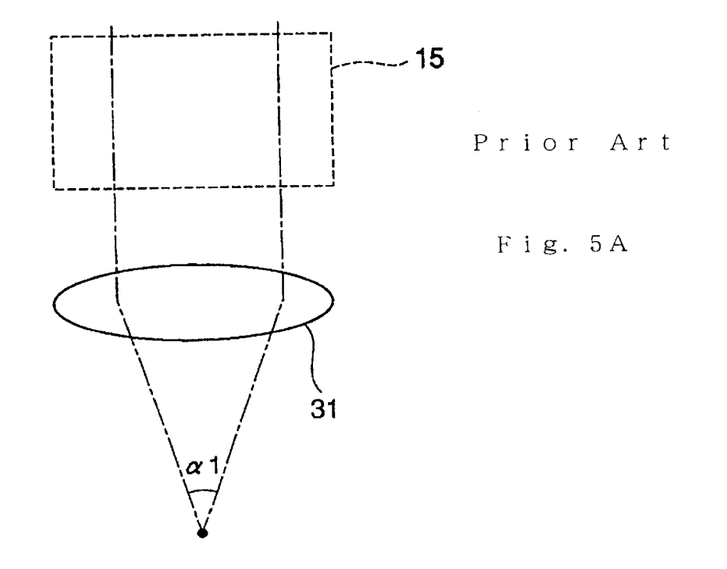
FIG. 5A is a schematic view in the case where the stereo angle converting portion of the stereo angle converting unit provided in the stereomicroscope of the slit lamp microscope which is one conventional example of the ophthalmologic apparatus which is not disposed on the right and left optical axes.
Figure 5B:
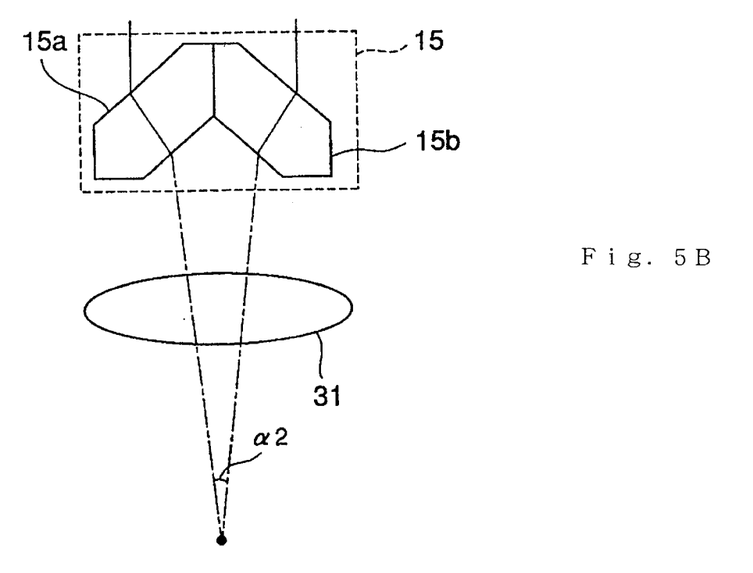
FIG. 5B is a schematic view in the case where the stereo angle converting portion is disposed on the right and left optical axes in FIG. 5A.
Figure 6:
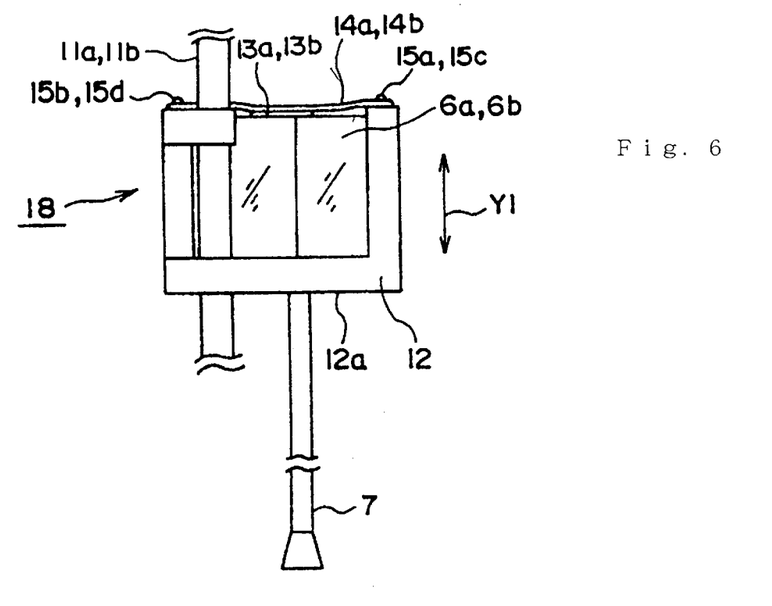
FIG. 6 is another side view representing the structure of the stereo angle converting portion of the stereo angle converting unit of the stereomicroscope according to the first embodiment of the present invention.

FIG. 4 is a plan view representing a structure of a stereo angle converting portion of a stereo angle converting unit of the stereomicroscope according to a first embodiment of the present invention, and FIGS. 5 and 6 are side views representing the structure of the stereo angle converting portion of the stereo angle converting unit of the stereomicroscope according to the first embodiment of the present invention. By the way, FIG. 5 shows the case where the stereo angle converting portion as shown in FIG. 4 is viewed from the direction represented by an arrow A1. Also, FIG. 6 shows the case where the stereo angle converting portion as shown in FIG. 4 is viewed from the direction represented by an arrow A2. As shown in FIGS. 4, 5 and 6, the stereo angle converting portion 18 has, prisms 6a and 6b for a stereo angle conversion, a setting member 12 on which the prisms 6a and 6b are set on, and a moving lever 7 for moving the stereo angle converting portion 18 in the up and down directions Y1.

As shown in FIG. 4, the prisms 6a and 6b each have the same shape, are constructed to be combined with each other by line-symmetrically adhering the prism 6a to the prism 6b with respect to one surface using an adhesive or the like, and are set on the setting member 12. Also, the prisms 6a and 6b are held by prism holding plates 14a and 14b through prism holding pads 13a and 13b. By the way, the prism holding pads 13a and 13b are constructed by a rubber or the like, and used as contact parts to the prisms 6a and 6b. Further, the prism holding plates 14a and 14b are used as parts for preventing positional shifts of the prisms 6a and 6b. Prism holding plate fixing screws 15a, 15b, 15c and 15d are attached to each of end portions of the prism holding plates 14a and 14b. The prism holding plate fixing screws 15a, 15b, 15c and 15d are used as parts for fixing the prism holding plates 14a and 14b to the prisms 6a and 6b. The moving lever 7 is attached to a bottom surface 12a of the setting member 12, and formed downward from the bottom surface 12a with a stick shape. The stereo angle converting portion 18 is moved along supports 11a and 11b in the up and down directions Y1 with the movement of the moving lever 7 in the up and down directions Y1, and thus disposed on the right and left optical axes L1 and L2.

As described above, the stereo angle converting portion 18 of the stereo angle converting unit 15 is inserted into or removed from the right and left optical axes L1 and L2 of the observation light fluxes with respect to the up and down directions (vertical direction) in accordance with a necessary stereo angle. Thus, (1) in a normal observation (a stereo angle is α1), since the stereo angle converting portion 18 of the stereo angle converting unit 15 is removed from the right and left optical axes in a position where the observation light fluxes are not shifted, an unnecessary optical member is not disposed on the right and left optical axes L1 and L2, so that a further distinct observation image can be obtained. (2) Also, since a high grade precision (perpendicularity) of parts is not required with respect to the prisms 6a and 6b of the stereo angle converting portion 18, which influences the shift of the right and left optical axes L1 and L2, optical parts can be simplified. (3) Further, in a stereo angle conversion by the stereo angle converting portion 18 of the stereo angle converting unit 15, a rotation mechanism for rotating optical parts for a stereo angle conversion, which is provided in a conventional optical system is not required. Thus, the rotation adjustment mechanism which influences the shift of the right and left optical axes is not required, so that a mechanism for a stereo angle conversion can be simplified.

The stereo angle converting unit of the stereomicroscope according to the first embodiment of the present invention is constructed as mentioned above, and performs a stereo angle conversion by inserting or removing the stereo angle converting portion into or from the right and left optical axes. However, a stereo angle converting unit having a plurality of stereo angle converting portions each with different stereo angles, as mentioned below, may be used. When such a stereo angle converting unit is used, since a stereo angle option is broadened if necessary, an observation and an examination with respect to the eye of the person to be examined can be easily performed.

Figure 7:
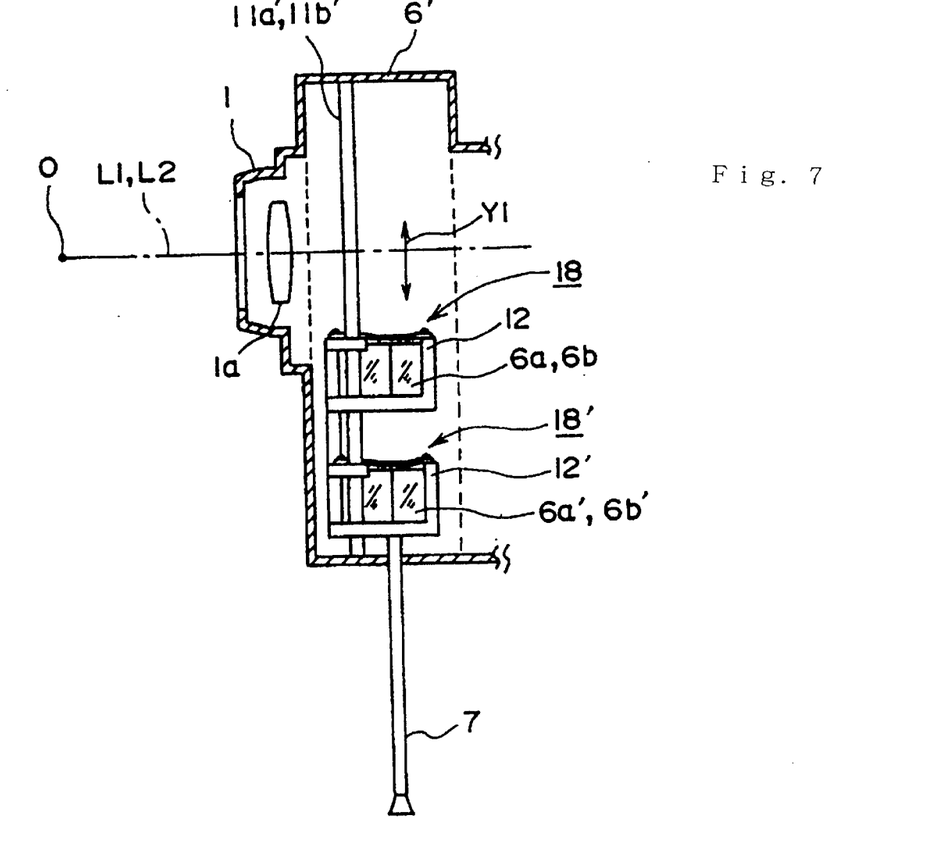
FIG. 7 is a schematic view representing a second embodiment of a structure of a stereo angle converting unit of the stereomicroscope according to the present invention.

FIG. 7 is a schematic view representing a structure of a stereo angle converting unit according to a second embodiment of the stereomicroscope of the present invention. In FIG. 7, a stereo angle converting unit 6' having a plurality of (in this embodiment, two) stereo angle converting portions 18 and 18' is provided in the stereomicroscope 6. The stereo angle converting portion 18' has the same structure as that of the stereo angle converting portion 18, and is constructed by prisms 6a' and 6b' for converting a stereo angle into other stereo angle different from the stereo angle (for example α2 is 4.5°) converted by the prisms 6a and 6b, a setting member 12' in which the prisms 6a' and 6b' are set on, and the like. Also, both end portions of supports 11a' and 11b' are provided fixedly on upper and lower inner side surfaces of the stereo angle converting unit 6', so that the stereo angle converting portion 18' can be moved in the up and down directions Y1. Thus, the moving lever 7 is made to move upwardly in accordance with a stereo angle necessary to observe and examine the eye of the person to be examined, so that the stereo angle converting portion 18' is moved along the supports 11a' and 11b' upwardly and thus disposed on the right and left optical axes L1 and L2.

Figure 8:
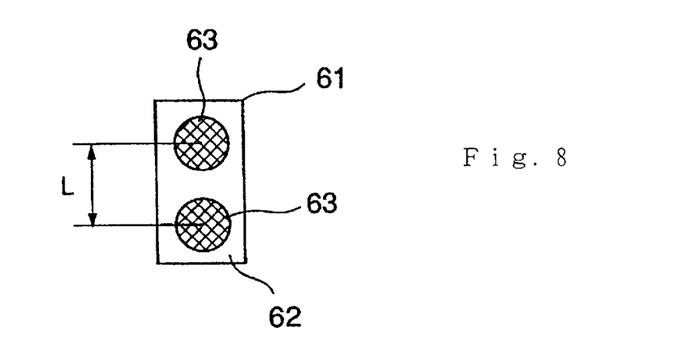
FIG. 8 shows a structure of a color temperature converting element provided in the stereomicroscope of the slit lamp microscope which is one example of the ophthalmologic apparatus according to the embodiment of the present invention.

FIG. 8 shows a structure of a color temperature converting element provided in the stereomicroscope of the slit lamp microscope which is one example of the ophthalmologic apparatus according to the embodiment of the present invention. As shown in FIG. 8, the color temperature converting element 61 is constructed by a substrate 62 and two color temperature converting filters 63. The color temperature converting filters 63 are formed with a predetermined interval (a center interval is an interval corresponding to the optical axis interval distance L between the right and left optical axes L1 and L2) on the substrate 62. Such constructed color temperature converting element 61 is inserted into or removed from the right and left optical axes L1 and L2, so that an optimum conversion of a color temperature of the observation light can be conducted in accordance with observation regions (front eye portion and eye fundus portion) of the eye E to be examined.

Figure 9:
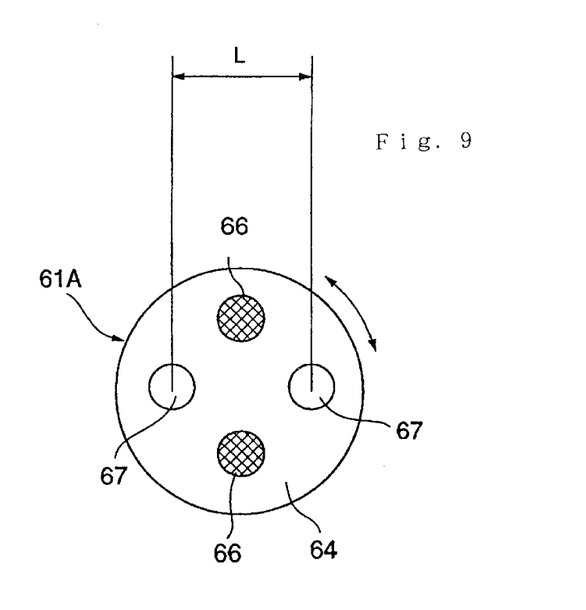
FIG. 9 shows another structure of a color temperature converting element provided in the stereomicroscope of the slit lamp microscope which is one example of the ophthalmologic apparatus according to the embodiment of the present invention.

Also, instead of the color temperature converting element 61 constructed as shown in FIG. 8, a color temperature converting element 61A constructed as shown in FIG. 9 can be used. That is, the color temperature converting element 61A is constructed by a rotation substrate 64, two color temperature converting filters 66 and two holes 67, both formed on the rotation substrate 64. By the way, in the color temperature converting element 61A, two color temperature converting filters 66 are formed with the interval corresponding to the above optical axis interval distance L on the rotation substrate 64. Also, two holes 67 are formed with the interval corresponding to the optical axis interval distance L in a position where the two holes 67 are rotated in respect to the two color temperature converting filters 66 by 90°.

For example, in the case where a front eye portion of the eye E to be examined is observed, the rotation substrate 64 is rotated such that two holes 67 of the color temperature converting element 61A are located on the right and left optical axes L1 and L2. On the other hand, in the case where an eye fundus portion of the eye E to be examined is observed, the rotation substrate 64 is rotated such that two color temperature converting filters 66 are located on the right and left optical axes L1 and L2. That is, the rotation substrate 64 may be rotated by 90° between the case where the front eye portion is observed and the case where the eye fundus portion is observed. Thus, an optimum conversion of a color temperature of the observation light can be conducted in accordance with observation regions (front eye portion or eye fundus portion) of the eye E to be examined.

Figure 10:
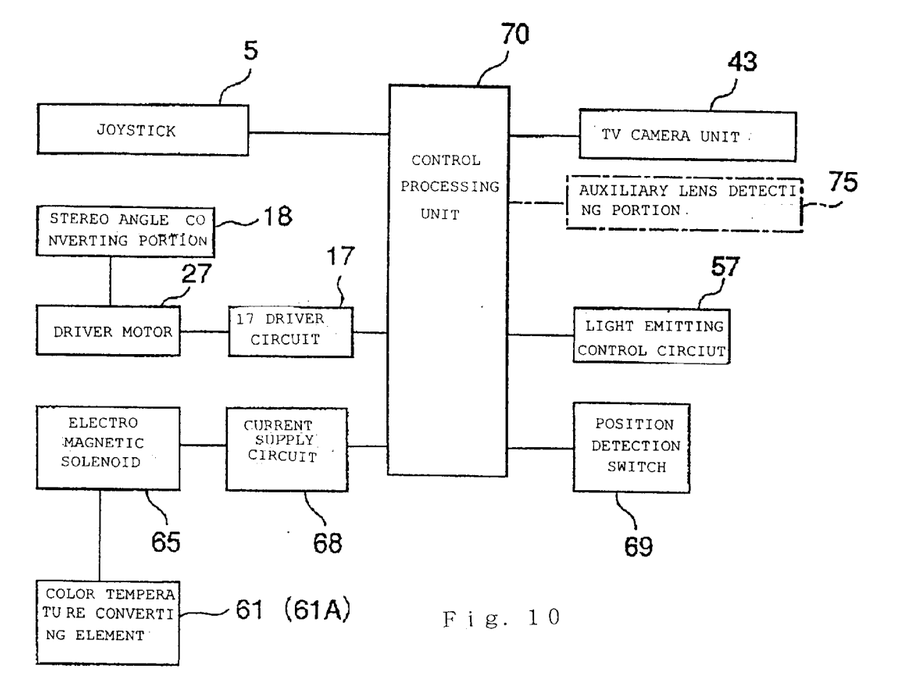
FIG. 10 is a block diagram representing a portion of the structure of the slit lamp microscope which is one example of the ophthalmologic apparatus according to the embodiment of the present invention.

FIG. 10 is a block diagram representing a portion of the structure of the slit lamp microscope which is one example of the ophthalmologic apparatus according to the embodiment of the present invention. As shown in FIG. 10, the ophthalmologic apparatus according to the embodiment of the present invention comprises the joystick 5, a driver circuit 17 for driving a driving motor 27, a TV camera unit 43, an electromagnetic solenoid 65 for inserting and removing the color temperature converting element 61 into and in respect to the right and left optical axes L1 and L2, a current supply circuit 68 for supplying a current to drive the electromagnetic solenoid 65, a light emitting control circuit 57 for performing light emitting control of a halogen lamp 51 and a xenon lamp 56, a position detection switch 69 for detecting a position of the frame 4, and a control processing unit 70 for controlling operations of the driver circuit 17, the TV camera unit 43, the light emitting control circuit 57 and the current supply circuit 68.

Generally, in the case where a front eye portion of the eye E to be examined is observed by using the ophthalmologic apparatus such as the slit lamp microscope according to the embodiment of the present invention, it is necessary to make the stereomicroscope 6 to approach the eye E to be examined by moving the frame 4 to the side of a person to be examined. On the other hand, in the case where an eye fundus portion of the eye E to be examined is observed, it is necessary to make the stereomicroscope 6 leave the eye E to be examined by moving the frame 4 from the side of the person to be examined to the side of the examiner. Thus, the position detection switch 69 is used to determine whether an observation region of the eye E to be examined by the examiner is the front eye portion or the eye fundus portion by detecting a moving position of the frame 4.

As described above, a movable region of the frame 4 is divided into two regions, that is, a first region which is near the eye E to be examined and in which the frame 4 is located in the case where the front eye portion is observed, and a second region which is further from the eye E to be examined than the first region and in which the frame 4 is located in the case where the eye fundus portion is observed. The position detection switch 69 is provided in a boundary region between the first region and the second region. For example, the position detection switch 69 is constructed so as to turn on when the frame 4 is located within the first region and to turn off when the frame 4 is located within the second region.

The control processing unit 70 determines whether the frame 4 is located within the first region or the second region by detecting an on/off state of the position detection switch 69 provided with the above structure. Also, the control processing unit 70 determines whether a stereo angle conversion by the stereo angle converting portion 18 is required or not and whether a color temperature conversion of observation light by the color temperature converting element 61 is required or not.

When it is determined that the stereo angle conversion is required, the control processing unit 70 controls the operation of the driver circuit 17 to drive the driving motor 27, so that a reed screw shaft 26 is moved in the up and down directions Y1 to insert or remove the stereo angle converting portion 18 onto or from the right and left optical axes L1 and L2. Also, when it is determined that the color temperature conversion of the observation light is required, the control processing unit 70 controls the operation of the current supply circuit 68 to supply a current, so that the electromagnetic solenoid 65 is moved to insert or remove the color temperature converting element 61 onto or from the right and left optical axes L1 and L2.

Next, the operation of the ophthalmologic apparatus according to the embodiment of the present invention will be described.

For example, when the front eye portion of the eye E to be examined is observed, the examiner operates the joystick 5 such that the frame 4 approaches the eye E to be examined. Here, when the frame 4 is located within the first region, the position detection switch 69 is turned on to output an ON-signal to the control processing unit 70.

When the ON-signal from the position detection switch 69 is received, the control processing unit 70 controls the operation of the driver circuit 17 to drive the driving motor 27. Thus, since the reed screw shaft 26 coupled with the driving motor 27 is moved downwardly, the stereo angle converting portion 18 is removed from the right and left optical axes L1 and L2 to convert the stereo angle of the stereomicroscope 6 to $\alpha 1$.

Also, the control processing unit 70 controls the operation of the current supply circuit 68 to supply a current from the current supply circuit 68 to the electromagnetic solenoid 65. Thus, the electromagnetic solenoid 65 is moved and then the color temperature converting element 61 is removed from the right and left optical axes L1 and L2.

By the above operation, after the stereo angle conversion of the stereomicroscope and the color temperature conversion of the observation light are completed, the control processing unit 70 controls the operation of the light emitting control circuit 57 such that the halogen lamp 51 emits light. Thus, the observation of the front eye portion of the eye E to be examined can be optimized.

On the other hand, for example, when the eye fundus portion of the eye E to be examined is observed, the examiner operates the joystick 5 such that the frame 4 farthers away from the eye E to be examined. Here, when the frame 4 is moved from the first region to the second region, the position detection switch 69 is turned off to output an OFF-signal to the control processing unit 70.

When the OFF-signal from the position detection switch 69 is received, the control processing unit 70 controls the operation of the driver circuit 17 to drive the driver motor 27. Thus, since the reed screw shaft 26 coupled with the driver motor 27 is moved upwardly, the stereo angle converting portion 18 is inserted into the right and left optical axes L1 and L2 and disposed to convert the stereo angle of the stereomicroscope 6 from $\alpha 1$ to $\alpha 2$.

Also, the control processing unit 70 controls the operation of the current supply circuit 68 to supply a current from the current supply circuit 68 to the electromagnetic solenoid 65. Thus, the electromagnetic solenoid 65 is moved and then the color temperature converting element 61 is inserted and disposed onto the right and left optical axes L1 and L2.

By the above operation, after the stereo angle conversion of the stereomicroscope and the color temperature conversion of the observation light are completed, the control processing unit 70 controls the operation of the light emitting control circuit 57 such that the halogen lamp 51 emits light. Thus, the observation of the eye fundus portion of the eye E to be examined can be optimized.

In the embodiment of the present invention as explained above, the stereo angle converting portion of the stereo angle converting unit is inserted into or removed from the right and left optical axes to perform the conversion of the stereo angle of the stereomicroscope. However, for example, a stereo angle converting unit can be constructed so that an optical element (for example, a prism) constituting a stereo angle converting portion is disposed on the right and left optical axes and then rotated for the stereo angle conversion.

Also, in the present invention, a stereo angle converting unit having a plurality of stereo angle converting portions with different stereo angles may be used. When such a stereo angle converting unit is used, since a stereo angle option is broadened when necessary, an observation and a photographing with respect to the eye of the person to be examined can be easily performed.

In the above embodiment, an insertion or a removal with respect to each of the optical elements is controlled by detecting a position of the frame, which is shifted in a front eye portion observation or in an eye fundus portion observation. Further, as shown by a broken line of FIG. 8, an auxiliary lens detecting portion 75 for detecting whether an auxiliary lens to be inserted between the eye to be examined and the objective lens is inserted or not is provided, and then an insertion or a removal with respect to each of the optical elements may be controlled based on a detection result of the auxiliary lens detecting portion.

In this case, the auxiliary lens detecting portion may detect a position of the auxiliary lens by processing an image obtained by, for example, a CCD camera of the TV camera unit 43. Also, the auxiliary lens detecting portion may be constructed such that a position of the auxiliary lens AL is detected by processing an output of a sensor provided in a position where the auxiliary lens AL is inserted on the right and left optical axes. Further, a switch for controlling switching of the stereo angle converting portion and the color temperature converting element is provided in the vicinity of the forehead rest 10b, and then the switch may be manually turned on or off when the auxiliary lens AL is inserted onto the optical axes. In the case where the switch is provided, if the front eye portion observation is performed in the switch-off and the eye fundus portion observation is performed in the switch-on, an advantage that the optical parts are necessarily inserted onto the optical axes in the eye fundus portion observation is obtained.

Also, in the above embodiment, the stereo angle is made small when the stereo angle converting element is inserted onto the right and left optical axes. However, it is needless to say that, an optical element may be used in which the stereo angle converting element is inserted onto the optical axes in the front eye portion observation, and then the stereo angle is made smaller when the stereo angle converting element is removed from the optical axes in the eye fundus portion observation.

Although the ophthalmologic apparatus of the present invention has been described in detail, the present invention is not limited to the above embodiment, but various improvements and modifications may be naturally made in the scope not departing from the gist of the present invention.

What is claimed is:

1. An ophthalmologic apparatus including a stereomicroscope, which is provided on a movable frame and in which observation light is divided into right and left optical axes between an objective lens and an eyepiece, and a halogen lamp as a light source is characterized by comprising: means for optically changing an optical path, which is provided on the right and left optical axes; and means for electrically and/or optically changing the observation light, wherein an image of a portion of an eye to be examined is easily observed;
   wherein the means for optically changing the optical path is constructed by a stereo angle converting means which is inserted orthogonal to the right and left optical axes, for performing a stereo angle conversion by shifting a relative position of the right and left optical axes.

2. An ophthalmologic apparatus including a stereomicroscope, which is provided on a movable frame and in which observation light is divided into right and left optical axes between an objective lens and an eyepiece, and a halogen lamp as a light source is characterized by comprising: means for optically changing an optical path, which is provided on the right and left optical axes; and means for electrically and/or optically changing the observation light, wherein an image of a portion of an eye to be examined is easily observed;
   wherein the means for optically changing the observation light is a color temperature converting element which is inserted in an observation light.

3. An ophthalmologic apparatus including a binocular stereomicroscope which is provided on a movable frame and divides an observation light in right and left optical axes is characterized by comprising;
   a stereo angle converting means for shifting a relative position of the right and left optical axes;
   a position detecting means for detecting the position of the frame; and
   a control means for controlling the operation of the stereo angle converting means in accordance with a result by the position detecting means.

4. An ophthalmologic apparatus including an illuminating means for illuminating an eye to be examined and a binocular stereomicroscope with right and left optical axes, both of which are provided on a movable frame is characterized by comprising:
   a stereo angle convening means for performing a stereo angle conversion by shifting a relative position of the right and left optical axes;
   a color temperature converting means for performing a conversion of a color temperature of the light reflected from the eye to be examined, which is illuminated by the illuminating means;
   a position detecting means for detecting a position of the frame; and
   control means for controlling operation of the stereo angle converting means and the color temperature converting means in accordance with a result by the position detecting means.

5. An ophthalmologic apparatus in which an auxiliary lens is to be inserted in or removed front optical axis between an eye to be examined and an objective lens in accordance with the time of observation of an eye fundus portion to be examined or a front eye portion observation is characterized by comprising:
   a detecting means for detecting an insertion of the auxiliary lens which is provided between the eye to be examined and the objective lens, and a control means for controlling an insertion and a removal of the stereo angle converting means and/or color temperature convening means in accordance with a result of the detecting means.

6. An ophthalmologic apparatus including a stereomicroscope, which is provided on a movable frame and in which observation light is divided into right and left optical axes between an objective lens and an eyepiece, and a halogen lamp as a light source is characterized by comprising: means for optically changing an optical path, which is provided on the right and left optical axes; and means for electrically and/or optically changing the observation light wherein an image of a portion of an eye to be examined is easily observed;
   wherein the means for optically changing the observation light is a color temperature converting element which is inserted in an observation light;

wherein the color temperature converting element is provided to be insertable in and &I removable from the observation light or an illumination light.

7. An ophthalmologic apparatus including a stereomicroscope, which is provided on a movable frame and in which observation light is divided into right and left optical axes between an objective lens and an eyepiece, and a halogen lamp as a light source is characterized by comprising: means for optically changing an optical path, which is provided on the right and left optical axes; and means for electrically and/or optically changing the observation light, wherein an image of a portion of an eye to be examined is easily observed;

wherein the means for electrically changing the observation light is a light source voltage control means for controlling a voltage up or down for the halogen lamp in accordance with the portion of the eye to be examined;

wherein the portion of the eye to be examined is a front eye portion or an eye fundus portion;

wherein the apparatus comprises further a switching means for alternately switching a light source voltage control between the front eye portion observation and the eye fundus portion observation, and the color temperature convening element is removed from an optical path of the light source when the light source voltage control is switched to the front eye portion observation, and the color temperature converting element is inserted into the light source when the light source voltage control is switched to the eye fundus portion observation.

8. In an ophthalmologic apparatus comprising a binocular stereomicroscope which is provided on a movable frame and divides an observation light into right and left optical axes, wherein the apparatus is characterized by comprising:

a stereo angle converting means being inserted perpendicularly to the right and left optical axes for converting the stereo angle for shifting a relative position;

a position detecting means for detecting the position of the frame; and a control means for controlling the operation of the stereo angle convening means in accordance with a result by the position detecting means.

9. In an ophthalmologic apparatus comprising a binocular stereomicroscope which is provided on a movable frame and divides an observation light into right and left optical axes according to claim 8, wherein the apparatus is characterized by comprising further an lluminating means for illuminating an eye to be examined;

a color temperature convening means for performing a conversion of a color temperature of the light reflected from the eye to be examined, which is illuminated by the illuminating means; and the position detecting means for detecting the position of the frame controls thither the operation of the color temperature convening means.

10. The ophthalmologic apparatus according to claim 9, wherein the color temperature convening means is provided to be insertable in and removable from an observation light path or the reflected path of an illuminating light.

11. In an ophthalmologic apparatus comprising a binocular stereomicroscope which divides an observation light into right and left optical axes and moves universally, wherein the apparatus is characterized by comprising:

a stereo angle converting means being inserted perpendicularly to the right and left optical axes for convening the stereo angle for shifting a relative position;

a position detecting means for detecting the position of the stereomicroscope;

a control means for controlling the operation of the stereo angle converting means in accordance with a result byte position detecting means;

an auxiliary lens is to be inserted in and removed from an axis between an eye to be examined and an objective lens in accordance with time of the observation of an eye fundus portion to be examined and an eye anterior portion to be examined;

a detecting means for detecting an insertion and removal of the auxiliary lens; and a control means for controlling the operation of the stereo angle converting means in accordance with a result of the detecting means.

* * * * *